United States Patent [19]

Hakomori et al.

[11] Patent Number: 4,851,511
[45] Date of Patent: Jul. 25, 1989

[54] MONOCLONAL ANTIBODY THAT SPECIFICALLY BINDS TO DISIALOSYL LE$^a$

[75] Inventors: Sen-itiroh Hakomori, Mercer Island, Wash.; Yasuo Fukushi, Sendai, Japan; Edward D. Nudelman, Seattle, Wash.; Steven B. Levery, Seattle, Wash.

[73] Assignee: Fred Hutchinson Cancer Research Center, Seattle, Wash.

[21] Appl. No.: 824,172

[22] Filed: Jan. 30, 1986

[51] Int. Cl.$^4$ .................. C07K 15/00; C12N 5/00; G01N 53/00; A61K 43/00; A61K 39/00
[52] U.S. Cl. .................. 530/387; 530/389; 435/240.27; 435/7; 435/172.2; 424/11; 424/85.91; 424/85.8; 935/104; 935/110; 436/548
[58] Field of Search ............ 530/387, 389; 435/240.27; 935/104, 110; 436/548; 424/85.8

[56] References Cited

U.S. PATENT DOCUMENTS 4,485,093 11/1984 Runge ........................... 424/85
4,675,287 6/1987 Reisfeld et al. ................. 435/7

OTHER PUBLICATIONS

Fukushi, Y. et al., "Novel Fucolipids Accumulating in Human Adenocarcinoma. III. A Hybridoma Antibody (FH6) Defining a Human Cancer-Associated Di--fucoganglioside VI$^3$ Neu AcV$^3$III$^3$Fuc$_2$nLc$_6$." *Journal of Biological Chemistry* 259(16): 10511–10517, Aug. 25, 1984.

Nudelman et al., J. Biol. Chem. 257(21):12752–12756, 1982.
Pukel et al., J. Exp. Med. 155: 1133–1147, 1982.
Cahan et al., Proc. Natl. Acad. Sci. U.S.A., 79: 7629–7633, 1982.
Rauvala et al., Biochim. Biophys. Acta 531: 266–274, 1978.
Kundu et al., J. Biol. Chem. 258(22): 13857–13866, 1983.

*Primary Examiner*—Margaret Moskowitz
*Assistant Examiner*—Kay E. Cheney
*Attorney, Agent, or Firm*—Christensen, O'Connor, Johnson & Kindness

[57] ABSTRACT

Disialosyl Le$^a$ (IV$^3$NeuAcIII$^6$NeuAcIII$^4$FucLc$_4$), a novel human cancer-associated fucoganglioside that is highly immunogenic. Also, a hybridoma cell line (ATCC No. HB 8861) secreting a monoclonal IgG3 antibody (FH7) directed to disialosyl Le$^a$. The disialosyl Le$^a$ antigen was detected in various cancer tissues and their cell lines but was absent in various normal tissues and blood cells. Sera of patients with various cancers, particularly early cases of colonic and gastric cancers, showed an elevated disialosyl Le$^a$ antigen level, which subsequently decreased after surgical tumor removal.

13 Claims, 6 Drawing Sheets

MONOCLONAL ANTIBODY THAT SPECIFICALLY BINDS TO DISIALOSYL LE$^a$

This invention was made partly with Government support under Grant GM23100 from the National Institutes of Health. The Government has certain rights in this invention.

TECHNICAL FIELD

This invention relates to tumor-associated antigens and to hybridoma cell lines producing monoclonal antibodies useful for the detection and treatment of cancer.

BACKGROUND OF THE INVENTION

Oncogenic transformation accompanies dramatic changes in the chemical composition, metabolism, and organization of cell surface glycoconjugates. With the development of the monoclonal antibody approach, it has become apparent that many tumor-associated antigens are carbohydrates that are anomalously expressed not only in specific types of human cancer but also in normal cells and tissues at certain stages of the embryo and fetus and in a few normal unrelated adult cells. For a review, see Hakomori, S., et al., J.Natl.Cancer Inst. 71:231, 1983. Monosialosyl gangliosides such as monosialosyl Le$^a$, monosialosyl Le$^x$, monosialosyl dimeric Le$^x$, and di- or trimeric Le$^x$, each defined by a specific antibody, are typical of the oncodevelopmental antigens that are expressed in a large variety of human cancers derived from gastrointestinal, pulmobronchial, and mammary gland epithelia. Disialogangliosides GD$_3$ and GD$_2$, also defined by specific antibodies, have been identified as melanoma- or neuroblastoma-associated antigens. It would be advantageous to define other tumor-associated disialosyl gangliosides and to establish antibodies reactive specifically thereto.

SUMMARY OF THE INVENTION

The invention provides a novel human cancer-associated fucoganglioside, disialosyl Le$^a$ (IV$^3$NeuAcIII$^6$NeuAcIII$^4$FucLc$_4$), that is useful as an immunogen. Disialosyl Le$^a$ was isolated from four other disialogangliosides by high-performance liquid chromatography followed by preparative high-performance thin-layer chromatography with two solvent systems. The structure of the antigen was characterized by methylation analysis and enzymatic degradation, followed by examination of the degradation products with specific monoclonal antibodies, and determined to be:

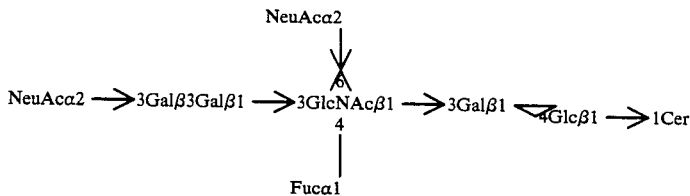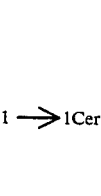

(1)

The disialosyl Le$^a$ antigen was detected in various cancer tissues and their cell lines but was absent in various normal tissues and blood cells. The disialosyl Le$^a$ antigen is highly immunogenic.

Also provided is a hybridoma cell line (ATCC No. HB 8861) secreting a monoclonal IgG3 antibody (FH7) directed to disialosyl Le$^a$. The hybridoma cell line was selected by reactivity of the FH7 antibody with disialosyl Le$^a$ and lack of reactivity with other glycolipids, including glycolipids having closely related structures, such as IV$^3$NeuAcIII$^4$FucLc$_4$, IV$^3$NeuAcnLc$_4$, IV$^6$-NeuAcnLc$_4$, and IV$^3$NeuAc$\alpha$2 →8NeuAcnLc$_4$. FH7 also reacts with an intermediate degradation product of disialosyl Le$^a$, namely monosialosyl Le$^a$II (III$^6$-NeuAcIII$^4$FucLc$_4$), which indicates that the antibody recognizes a GlcNAc structure fully substituted with $\beta1\rightarrow3$ galactosyl, $\alpha1\rightarrow4$ fucosyl, and $\alpha2\rightarrow6$ sialosyl:

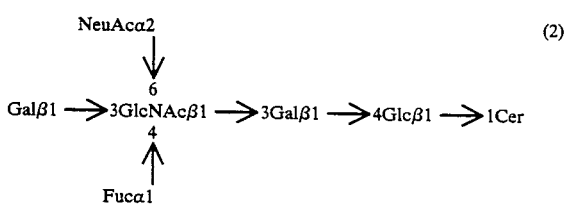

(2)

The antibody FH7 is highly reactive with a large variety of human cancer cells, particularly colonic and gastric adenocarcinoma, but does not react with a variety of normal cells, including normal colonic mucosa. Sera of patients with various cancers, particularly early cases of colonic and gastric cancers, showed an elevated level of disialosyl Le$^a$ antigen, which subsequently decreased after surgical tumor removal. Since the disialosyl Le$^a$ antigen recognized by the antibody FH7 is closely associated with human malignancy, FH7 is of practical value in diagnostic tests and in monitoring and implementing various cancer treatments.

DESCRIPTION OF THE PREFERRED EMBODIMENT

Figure 1:
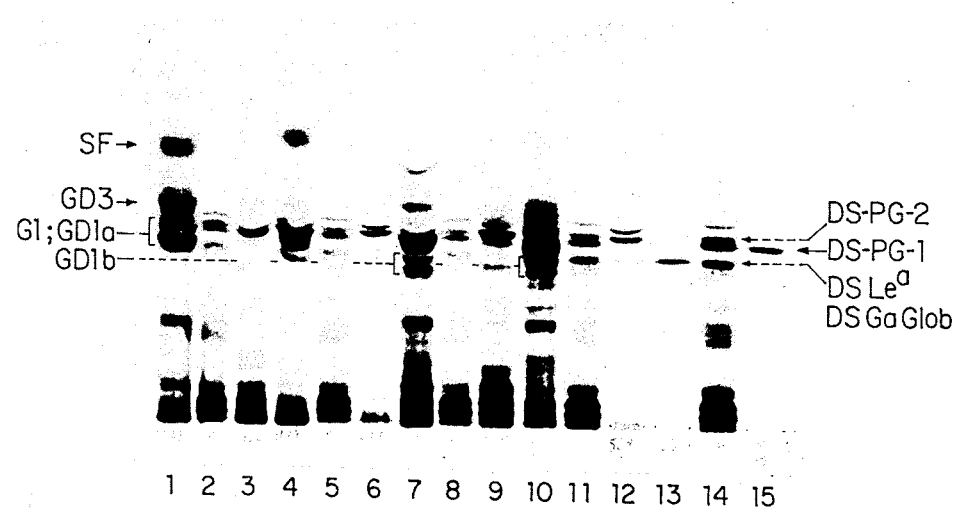
FIG. 1 shows the disialoganglioside fraction of various human adenocarcinoma and normal tissues.

Glycolipids are designated and abbreviated herein according to the recommendations of the Nomenclature Committee of the International Union of Pure and Applied Chemistry, as stated in Lipids 12:455–463, 1977; however, the suffix "-ose" is omitted for the shorthand designation. Ganglio-series are abbreviated according to Svennerholm, J.Lipid Res. 5:145–155, 1964. Case numbers of tumor tissues were given by the Tumor Procurement Program of the National Institutes of Health.

In contrast to the major tumor-associated glycolipid antigens previously described, the subject disialosyl $Le^a$ constitutes only a minor component of cancer tissue. The chemical quantity of disialosyl $Le^a$ glycolipid is so low that it is hardly detectable on high-performance thin-layer chromatography by orcinol-sulfuric acid reaction. As an approximate estimation, disialosyl $Le^a$ constitutes less than 0.1% of the chemical quantity of sialosyl $Le^x$ ganglioside and 5–10% of the chemical quantity of monosialosyl $Le^a$ antigen present in average colonic cancer tissue. Furthermore, the disialosyl $Le^a$ component exhibits the same chromatographic behavior as another minor disialoganglioside (disialosylgalactosyl globoside), and separation of disialosyl $Le^a$ and disialosylgalactosyl globoside was only possible on high-performance thin-layer chromatography with prolonged development in a propanol-ammonia system.

Disialosyl $Le^a$ displays a prominent immunogenicity to mice, and the hybridoma secreting IgG3 antibody designated FH7 has been established. Other disialogangliosides were less immunogenic, and no other antibodies were obtained under the same immunization-cell fusion protocol.

Since the chemical quantity of disialosyl $Le^a$ antigen was extremely small, its source was limited, and its separation required multi-step high-performance liquid chromatography (HPLC) and high-performance thin-layer chromatography (HPTLC), chemical characterization of this antigen based on standard established procedures was difficult. The quantity of the pure sample was not sufficient to perform compositional analysis of sugars, NMR analysis, or methylation analysis of the enzyme-degraded product. However, sialidase or weak acid degradation, comparison of immunoblotting activity of the enzyme-degraded products, and methylation analysis clearly support the structure of the disialosyl $Le^a$ antigen:

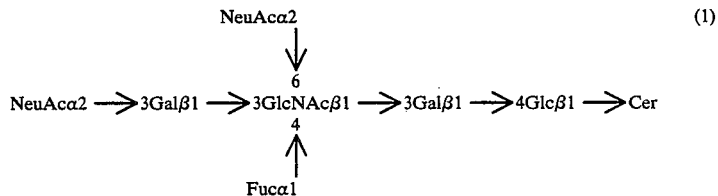

(1)

The disclosed disialosyl $Le^a$ fucoganglioside and its monosialo $Le^a$II derivative are considered useful immunogens. Hybridoma cell line ATCC No. HB 8861 expresses an IgG3 monoclonal antibody (FH7) that is directed specifically to the disialosyl $Le^a$ antigen. FH7 also reacts with monosialo $Le^a$II ($III^6NeuAcIII^4FucLc_4$), but does not specifically react with $IV^3NeuAcIII^4FucLc_4$, $IV^3NeuAcnLc_4$, $IV^6NeuAcnLc_4$, or $IV^3NeuAc\alpha2 \to 8NeuAcnLc_4$. See TABLE 1 and Examples 4 and 5.

TABLE 1

Mono- and disialosyl $Le^a$ and their related antigens defined by various monoclonal antibodies

| | Structure identified | FH7 | N-19-9 or CSLEA-1 | C4-11 |
|---|---|---|---|---|
| (A) Disialo $Le^a$ | $SAc2 \downarrow 6$ <br> $SA\alpha2 \to 3GAl\beta1 \to 3GlcNAc\beta1 \to 3Gal \to R$ <br> $4 \uparrow$ <br> $Fuc\alpha1$ | +++ | − | − |
| (B) Monosialo $Le^aI$ | $SA\alpha2 \to 3GAl\beta1 \to 3GlcNAc\beta1 \to 3Gal \to R$ <br> $4 \uparrow$ <br> $Fuc\alpha1$ | − | +++ | − |
| (C) Monosialo $Le^aII$ | $SAc2 \downarrow 6$ <br> $GAl\beta1 \to 3GlcNAc\beta1 \to 3Gal \to R$ <br> $4 \uparrow$ <br> $Fuc\alpha1$ | ++ | − | ++ |

TABLE 1-continued
Mono- and disialosyl Le$^a$ and their related antigens defined by various monoclonal antibodies

| Structure identified | FH7 | N-19-9 or CSLEA-1 | C4-11 |
|---|---|---|---|

(D) Le$^a$ $$\begin{array}{c} \text{GAl}\beta1 \longrightarrow \text{3GlcNAc}\beta1 \longrightarrow \text{3Gal} \longrightarrow \text{R} \\ 4 \\ \uparrow \\ \text{Fuc}\alpha1 \end{array}$$

FH7: —   N-19-9/CSLEA-1: —   C4-11: +++

(E) Disialosyllactotetraosylceramide $$\begin{array}{c} \text{SAc2} \\ \downarrow \\ 6 \\ \text{SA2} \longrightarrow \text{3GAl}\beta1 \longrightarrow \text{3GlcNAc}\beta1 \longrightarrow \text{3Gal}\beta1 \longrightarrow \text{4Glc} \longrightarrow \text{Cer} \end{array}$$

FH7: —   N-19-9/CSLEA-1: ND   C4-11: ND

The subject disialosyl Le$^a$ antigen reacted with FH7 but did not react with anti-Le$^a$ antibody C4-11, which requires an unsubstituted Gal$\beta1\rightarrow$3GlcNAc as well as Fuc$\alpha1\rightarrow$4GlcNAc. Nor was disialosyl Le$^a$ reactive with sialosyl Le$^a$ antibodies N-19-9 or CSLEA-1. NeuAc$\alpha2\rightarrow$6GlcNAc substitution obviously inhibited the reactivity of sialosyl Le$^a$I (NeuAc$\alpha2\rightarrow$3Gal$\beta1\rightarrow$3-[Fuc$\alpha1\rightarrow$4]GlcNAc) to N-19-9 antibody. Interestingly, the sialosyl residue linked to the Gal residue can be readily released by hydrolysis with *Clostridium perfringense* sialidase in the absence of detergent, resulting in an intermediate product:

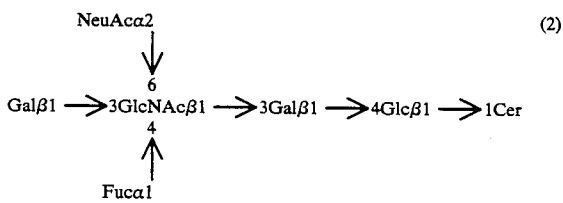

(2)

This intermediate compound was isolated and characterized by (i) identical thin-layer chromatography (TLC) mobility as monosialosyl Le$^a$I, defined by N-19-9 antibody, (ii) reactivity with anti-Le$^a$ antibody C4-11, (iii) reactivity with FH7 antibody, (iv) nonreactivity with N-19-9 antibody, and (v) conversion to Le$^a$-active ceramide pentasaccharide by Arthrobacter sialidase, which can hydrolyze NeuAc$\alpha2\rightarrow$6GlcNAc residue, or by acetic acid treatment. The positive reactivity of FH7 with this intermediate compound clearly indicates that FH7 requires NeuAc$\alpha2\rightarrow$6-substituted Le$^a$ antigen, which is hereby designated monosialosyl Le$^a$II. However, the monosialosyl Le$^a$II structure is absent in naturally occurring glycolipids, since the monosialoganglioside fraction of tumor extracts did not show any reactivity with FH7, and disialosyl Le$^a$ is the sole antigen detectable with FH7.

Sialosyl Le$^a$ defined by the monoclonal antibodies N-19-9 and CSLEA-1 has been well established as a human tumor-associated antigen highly expressed in colorectal, gastrointestinal, and pancreatic cancer. The sialosyl Le$^a$ antigen level in patients with cancer is significantly higher than that in noncancerous and normal subjects. More recently, the sialosyl Le$^a$ antigen was found in high quantity in seminal fluid, although its expression in normal tissue is otherwise limited to gall bladder epithelia, ductal epithelia of pancreas, and salivary glands. The subject disialosyl Le$^a$ antigen is closely related to sialosyl Le$^a$ defined by antibodies N-19-9 and CSLEA-1, i.e., one extra sialic acid is attached to the sixth position of the GlcNAc residue of sialosyl Le$^a$ structure. The significance of the disialosyl Le$^a$ antigen as a putative tumor marker is clear, since positive immunostaining with FH7 of the disialoganglioside fraction extracted from various tumor tissues and negative immunostaining of the same fraction from normal tissues and normal blood cells have been demonstrated.

The antibody FH7 is highly reactive with a variety of human cancer cells, particularly colonic and gastric adenocarcinoma, but is essentially unreactive with various normal tissues and blood cells, including normal colonic mucosa. Of 18 tumor extracts examined by immunostaining, eight showed the presence of a disialosyl Le$^a$ as defined by its specific monoclonal antibody FH7. The tumor TG126 (colonic adenocarcinoma metastatic to liver) contained the highest quantity of the antigen, and so the isolation and characterization of disialosyl Le$^a$ described below was based on that tumor sample. No antigen was detected in normal blood cells (erythrocytes, granulocytes, lymphocytes), liver, gastrointestinal, and colorectal tissue extracts.

Since the disialo Le$^a$ antigen defined by FH7 is a useful marker of cancer, the antibody FH7 is of practical value in diagnostic tests and in monitoring and implementing various cancer treatments. For example, the antibody FH7 can be coupled to a radionuclide and introduced into the body of a mammal to image cancer cell location and/or implement radiotherapy. The antibody FH7 can be similarly conjugated with an antitumor drug for cancer therapy. The monoclonal antibody FH7 can also be coupled to a detectable marker for immunohistological detection of cells that express the disialosyl Le$^a$ ganglioside. The detectable marker can be selected from among fluorophores, enzymes, chromophores, coenzymes, chemiluminescent materials, enzyme inhibitors, paramagnetic metals such as gadolinium, and radionuclides that are known in the art. Explanted cells can then be contacted with the FH7-marker conjugate, and any detectable marker that becomes sequestered on the cells can be detected by standard techniques after unreacted antibody is washed away. Tumor-associated antigen can also be detected in blood serum using standard immunoassays but employing the antibody FH7. The FH7 antibody, as well as other antibodies raised against the disialosyl Le$^a$ antigen, can be packaged in diagnostic test kits for assaying the presence of disialosyl Le$^a$.

The following Examples are presented to illustrate the advantages of the present invention and to assist one of ordinary skill in making and using the same. The following Examples are not intended in any way to otherwise limit the scope of the disclosure or the protection granted by Letters Patent hereon.

EXAMPLE 1

Isolation of Disialosyl Le$^a$

Disialosyl Le$^a$ (IV$^3$NeuAcIII$^6$NeuAcIII$^4$FucLc$_4$; see TABLE 1, structure A), disialosyllactoneotetraosylceramide (IV$^3$NeuAc$\alpha$2→8NeuAc$\alpha$2→3nLc$_4$), and disialosyllactotetraosylceramide (IV$^3$NeuAcIII$^6$NeuAcLc$_4$; TABLE 1, structure E) were prepared from the disialoganglioside fraction of human adenocarcinoma by HPLC followed by further purification on HPTLC.

Tumor tissues, tumor cell lines, and glycolipid samples

Liver metastatic deposits from eighteen cases of various human cancers such as colonic, pancreas, breast, bladder, gall bladder, and testis were obtained from the Tumor Procurement Program of the National Institutes of Health. Some other primary tumor tissues, normal colonic mucosa, and normal liver tissue were obtained from the Department of Pathology, Swedish Hospital, Seattle, WA. The liver metastatic tissue from colon tumor case TG126 was determined to contain the highest quantity of the disialosyl Le$^a$ antigen, and this tumor sample was used for isolation and characterization of the antigen. The disialosyl Le$^a$ antigen was also prepared from human lung cancer cell lines QG-90 and QG-56. These cell lines were cultured in Dulbecco-modified Eagle's medium supplemented with 10% fetal calf serum.

Various gangliosides were prepared in this laboratory and were purified on HPLC. From human erythrocyte membranes and human cancer tissues were prepared: sialosyl 2→3 lactoneotetraosylceramide (sialosyl paraglobaside, IV$^3$NeuAcnLc$_4$) as described in Biochim.Biophys.Acta 330:147-155, 1973; sialosyl 2→6 lactoneotetraosylceramide (VI$^6$NeuAcnLc$_4$) (J.Biol.Chem. 254:8223-8229, 1979; J.Biol.Chem. 258:11819-11822, 1983); and sialosyl 2→3 lactonorhexaosylceramide (VI$^3$NeuAcnLc$_6$) (J.Biol.Chem. 254:8223-8229, 1979). The 6C ganglioside (VI$^6$NeuAcIII$^3$FucnLc$_6$) (Biochem.Biophys.Res.Commun. 113:791-798, 1983) and the 6B ganglioside (VI$^3$NeuAcV$^3$FucIII$^3$FucnLc$_6$) (J.Biol.Chem. 259:10511-10517, 1984) were prepared from the monosialoganglioside fraction of human colonic adenocarcinoma as previously described. Sialosyl Le$^a$ antigen (VI$^3$NeuAcIII$^4$FucLc$_4$; see TABLE 1, structure D) as described by Magnani et al. (J.Biol.Chem. 257:14365-14369, 1982) was prepared from the monosialoganglioside fraction of human adenocarcinoma. GD$_{Ia}$ and GD$_{Ib}$ gangliosides were prepared from bovine brain ganglioside fraction by chromatography on diethylaminoethyl-Sepharose (Methods Enzymol. 83:139-191, 1982) followed by purification on HPLC in an isopropanol-hexane-water system as described in J.Biol.Chem. 259:4672-4680, 1984; J.Lipid Res. 22:1020-1024, 1981. Disialosyllactoneotetraosylceramide (disialosyl type 2 chain paragloboside; IV$^3$NeuAc$\alpha$2→8NeuAcnLc$_4$) was prepared from human adenocarcinoma, although this ganglioside was previously prepared from human kidney by Rauvala et al. (Biochim.Biophys. Acta 531:266-274, 1978). Disialosyllactotetraosylceramide (disialosyl type 1 chain paragloboside; IV$^3$NeuAcIII$^6$NeuAcLc$_4$) was isolated from the disialoganglioside fraction of human colonic cancer tissue as described below. The disialosylgalactosyl globoside (IV$^3$NeuAc2→3[NeuAc2→6]GalGb$_4$) ganglioside was previously isolated and characterized from the disialoganglioside fraction of human erythrocyte membranes by Kundu et al. (J.Biol.Chem. 258:13857-13866, 1983). GD$_3$ ganglioside was prepared from the disialoganglioside fraction of human melanoma tissue (J.Biol.Chem. 257:12752-12756, 1982).

Extraction of Tissues and Subsequent Fractionation

Tissues were extracted three times by homogenizing with four volumes (w/v) of isopropanolhexane-water (55:25:20, v/v/v) (J.Biol.Chem. 259:4672-4680, 1984; J.Biol.Chem. 257:14865-14874, 1982), and the extracts were combined and evaporated to dryness. The dried residue was dissolved in chloroform-methanol (2:1, v/v) to a ratio of five times volume chloroform-methanol to the original tissue weight, followed by partition with water according to the procedure of Folch-Pi et al., J.Biol.Chem. 191:819-831, 1951. The Folch's upper phases after four repeated partitions with the theoretical upper phase (chloroform-methanol-0.1% NaCl, 1:10:10) (Glycolipid Methodology, L.A. Witting, ed., pp. 13-47, American Oil Chemist's Society, 1976) were combined, evaporated to a small volume (50 ml), dialyzed against distilled water in a Spectrapor dialysis tube (Spectrum Medical Industries, Los Angeles, CA) (J.Biol.Chem. 259:4672-4680, 1984; J.Biol.Chem. 259:10511-10517, 1984; J.Biol.Chem. 257:14865-14874, 1982), and evaporated in a rotary evaporator to a dryness. The residue was dissolved in chloroform-methanol-water (30:60:8, v/v/v) and loaded on a diethylaminoethyl-Sepharose column according to the procedure of Ledeen and Yu, Meth.Enzymol. 83:139-191, 1982. After the monosialo fraction was eluted with chloroform-methanol-water (30:60:8) containing 0.04 M ammonium acetate (J.Biol.Chem. 259:10511-10517, 1984), the disialoganglioside fraction was eluted with the same solvent containing 0.15 M ammonium acetate (Meth.Enzymol. 83:139-191, 1982). The monosialo and disialoganglioside fractions were dialyzed against distilled water, evaporated in a rotary evaporator, and lyophilized. A typical HPTLC pattern of the disialoganglioside fraction of various tumors is shown in FIG. 1A. The yield of disialoganglioside was approximately 65 μg of sialic acid per gram of tumor tissue, in contrast to 185 μg of sialic acid per gram of tumor found in the monosialoganglioside fraction.

FIG. 1 is a HPTLC chromatogram developed with n-propanol-water-concentrated ammonia (7:3:1, v/v/v) and visualized with 0.2% orcinol in 10% sulfuric acid. Lanes 1-15 are identified as follows: Lanes 2, 5, 8, 11 and 14, tumor TG126; lane 1, TG1028; lane 3, TG666; lane 4, TG979; lane 6, TG217; lane 7, TG075; lane 9, TG845; lane 10, disialoganglioside fraction of blood group A erythrocytes; lane 12, TG564; lane 13, purified disialosyl Le$^a$; and lane 15, disialosyllactotetraosylceramide. The positions of the following gangliosides are identified on the right margin: DSPG-2 represents disialosyl type 2 chain paragloboside (IV$^3$NeuAc$\alpha$2→8NeuAcnLc$_4$); DSPG-1 represents disialosyl type 1 chain paragloboside (disialosyllactotetraosylceramide; IV$^3$NeuAcIII$^6$NeuAcLc$_4$); DSLe$^a$ represents disialosyl Le$^a$ (IV$^3$NeuAcIV$^3$FucIII$^6$NeuAcLc$_4$); and DSGa- Glob represents disialosylgalactosyl globoside ($IV^3$-[NeuAc]$_2$GalGb$_4$). On the left margin, the positions of ganglio-series gangliosides GD3, GD1a, and GD1b are shown; and Sf represents sulfatide.

Figure 2:
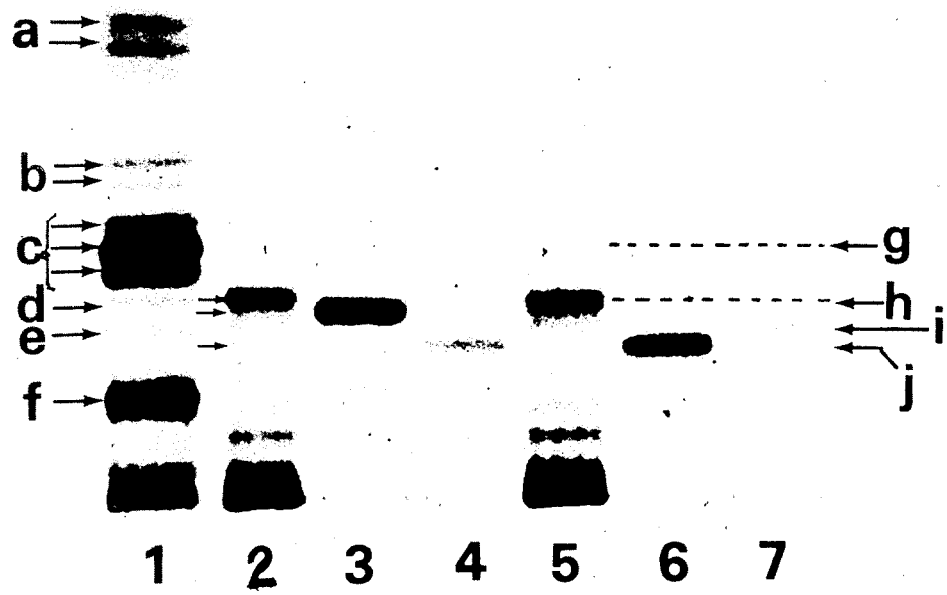
FIG. 2 shows high-performance thin-layer chromatograms of the ganglioside fraction of a representative colonic cancer tissue and the purified disialoganglioside fraction therefrom.

The disialoganglioside fraction of most of the tumors examined exhibited a pattern similar to that shown in FIG. 1. The fraction usually consists of GD$_3$ (FIG. 1, lanes 1 and 10; FIG. 2, band g, lanes 2 and 5), disialosyllactoneotetraosylceramide (disialosyl type 2 chain paraglobosíde) (FIG. 1, DS-PG-2; FIG. 2, lane 7, band i), disialosyllactotetraosylceramide (disialosyl type 1 chain paraglobosíde) (FIG. 1, DS-PS-1, lane 15), GD$_{la}$ ganglioside (FIG. 2, lanes 2 and 5, band h), disialosylgalactosyl globoside (FIG. 1; FIG. 2, lane 6), in addition to the subject disialosyl Le$^a$ antigen (FIG. 1, lane 13; FIG. 2, lane 4). The two fast-migrating components, disialosyllactoneotetraosylceramide and disialosyllactotetraosylceramide, were separated on prolonged development in chloroform-methanol-water. Disialosylgalactosyl globoside and disialosyl Le$^a$ antigen comigrate as a slow-migrating single band (FIG. 2, band j) on HPTLC in most of the solvent systems consisting of chloroform-methanol-water with ammonia or CaCl$_2$. However, these two components were separated by HPTLC with prolonged development in a solvent of 1-propanol-water-28% ammonia (7:1:2.5, v/v/v). Thus, all these components were isolated as single bands on HPTLC (FIG. 2, lanes 4, 6 and 7).

Purification of disialogangliosides

The disialoganglioside fraction was lyophilized in a 50-ml round-bottom flask, 1 ml of chloroform-methanol (1:1) was added, and the mixture was warmed and sonicated. The solution was applied to a column of Iatrobeads 6RS-8010 (Iatron Chemical Co., Higashi-kanda, Chiyoda-ku, Tokyo) (1×50 cm) according to the method of Watanabe and Arao (J.Lipds Res. 22:1020–1024, 1981), as modified by Kannagi et al. (J.Biol.Chem. 257:14865–14874, 1982), i.e., the sample solution was injected onto the column of Iatrobeads 6RS-8010 which was washed and equilibrated with isopropanol-hexane-water (55:40:5, v/v/v). Gradient elution was performed from isopropanol-hexane-water (55:40:5, v/v/v) to isopropanol-hexane-water (55:20:25, v/v/v) employing a three-solvent Varian HPLC system during 300 min. followed by continuous elution with a constant solvent composition of isopropanol-hexane-water (55:20:25) for an additional 100 min. The total volume of solvent used for elution was 400 ml, collected over 100 tubes during 400 min. with a flow rate of 1.0 ml/min; thus, the eluate volume collected per tube was 4 ml. The pressure was automatically adjusted as 10–23 atmos/inch$^2$ during the elution program. Each fraction was analyzed by HPTLC developed with chloroform-methanol-water (60:40:9, v/v/v containing 0.02% CaCl$_2$). The pooled fractions containing gangliosides with similar TLC mobilities were combined and the fractions were numbered 1–6. Each fraction was characterized as containing the following components: fraction 1 (tubes 21–23), GD$_3$; fraction 2 (tube 24), fast-migrating component of GD$_{la}$; fraction 3 (tube 25), slower-migrating component of GD$_{la}$; fraction 4 (tubes 26–30), slowest-migrating component of GD$_{la}$; fraction 5 (tubes 31–37), a mixture of a component slower than GD$_{la}$ (identified as disialosyllactoneotetraosylceramide, $IV^3$NeuAc2→8NeuAcnLc$_4$), a component with a slightly slower mobility that was identified as disialosyllactotetraosylceramide ($IV^3$NeuAcIII$^6$NeuAcLc$_4$), and a part of the band containing disialosylgalactosyl globoside and disialosyl Le$^a$; fraction 6 (tubes 38–50), a part of disialosyllactotetraosylceramide and the major part of a band containing disialosylgalactosyl globoside and disialosyl Le$^a$. Since the disialogangliosides in fractions 5 and 6 were not separated by HPLC on Iatrobeads column, these fractions were pooled, and each component was separated by HPTLC as described below.

Further purification of disialogangliosides on HPTLC

The pooled fractions 5 and 6 above were first separated into fast-and slow-migrating bands on an HPTLC plate (Merck, Darmstadt, West Germany) developed with a solvent mixture of chloroform-methanol-water (60:40:9, v/v/v) containing 0.02% CaCl$_2$. The faster-migrating bands contained disialosyllactoneotetraosylceramide (disialosyl type 2 chain paraglobosíde; $IV^3$-NeuAcα2→8NeuAcnLc$_4$) and disialosyllactotetraosylceramide (disialosyl type 1 chain paraglobosíde; $IV^3$NeuAcIII$^6$NeuAcLc$_4$). The separation and characterization of these faster-migrating components are not pertinent to the present invention. The slower-migrating bands were found to be a mixture of disialosylgalactosyl globoside ($IV^3$NeuAc2→6[NeuAc2→3]GalGb$_4$) and disialosyl Le$^a$. These slower-migrating two components were separated on Merck HPTLC plate (10×20 cm) with a prolonged development with 1-propanol-water-28% ammonium hydroxide (7:2. 5:1). [The disialoganglioside fraction can be directly separated into components on preparative HPTLC without a preliminary separation by HPLC. However, the sample should be purified first on a hydrophobic column (e.g., "Bond Elut"$^{TR}$ C18; Analytichem International, Harbor City, CA).] Gangliosides were placed along a line on the 10 cm side, and developed for 3 hours towards the 20 cm side. Glycolipid bands were visualized by spraying with Primulin (Aldrich Chemical Co., Milwaukee, WI) and observed under UV light (Meth.Enzymol. 35:396–425, 1975). Positive bands were scraped from the HPTLC plate, extracted with isopropanol-hexane-water (55:25:20, v/v/v) with sonication for 5 min., and centrifuged. The silica gel precipitate was re-extracted three times, and the extracts were combined and evaporated to dryness, dissolved in a small quantity (200 μl) of isopropanol-hexane-water (50:25:20, v/v/v), and filtered through a MILLIPORE filter (Millipore Corporation, Bedford, MA) to eliminate silica gel particles. The filtrate was dried under nitrogen stream and analyzed without further treatment. The overall yield of disialosyl Le$^a$ was 30–50 μg per 100 g of tumor tissue. Other disialogangliosides were separated during the first step HPLC on Iatrobeads column, and their locations are shown in FIG. 2.

Referring to FIG. 2, lanes 1–7 are identified as follows: Lane 1, total monosialogangliosides; lanes 2 and 5, total disialogangliosides; lane 3, GD$_{la}$ (upper band) and GD$_{lb}$ (lower band) of human brain; lane 4, purified disialo Le$^a$ antigen; lane 6, purified disialosylgalactosylglobosíde; lane 7, purified disialosyllactoneotetraosylceramide. The positions of the following gangliosides are identified on the margins by reference letters a–j: Duplet a represents GM$_3$ ganglioside; duplet b, sialosyl 2→3 lactoneotetraosylceramide ($IV^3$NeuAcnLc$_4$); triplet c, sialosyl 2→3 lactoneotetraosylceramide ($IV^6$-NeuAcnLc$_4$); d, sialosyl 2→3 lactonorhexaosylceramide ($VI^3$NeuAcnLe$_6$) and sialosyl Le$^a$I antigen ($IV^3$-NeuAcIII$^4$FucLc$_4$); e, disialosyllactotetraosylceramide ($IV^3$NeuAcIII$^6$NeuAcLc$_4$); f, a mixture of 6B ganglioside (VI³NeuAcV³FucIII³FucnLc₆) and 6C ganglioside (VI³NeuAcV³FucIII³FucnLc₆) and 6C ganglioside (VI⁶NeuAcIII³FucnLc₆); g, GD₃ ganglioside; h, GD$_{la}$ ganglioside having a ceramide with long chain fatty acid; i, disialosyllactoneotetraosylceramid (VI³-NeuAc2→8NeuAcnLc₄); and j, disialosyl Le$^a$ and disialosylgalactosyl globoside (IV³NeuAc2→3-[NeuAc2→6] GalGb₄).

EXAMPLE 2

Characterization of Disialosyl Le$^a$

The isolated disialosyl Le$^a$ was characterized by methylation analysis with mass spectrometry, enzymatic degradation, and determination of the enzyme-degraded products by TLC and immunostaining with anti-Le$^a$ monoclonal antibody.

Methylation analysis

Glycolipids were methylated (J.Bio.Chem. 55:205–208, 1964) and hydrolyzed, and partially O-methylated hexitol and hexosaminitol acetate derivatives were prepared as described in J.Biol.Chem. 259:14773–14777, 1984; J.Biol.Chem. 259:8444–8451, 1984. The derivatives were analyzed by gas chromatography-chemical ionization mass spectrometry using selected ion monitoring under conditions that are a combination of various methods previously described (J.Biol.Chem. 259:14773–14777, 1984; J.Biol.Chem. 259: 8444–8451, 1984; Twenty-Seventh International Congress of Pure and Applied Chemistry, A. Varmavour, ed., pp. 193–198, Pergamon Press, N.Y., 1980; Carbohydr.Res. 56:239–248, 1977).

Figure 3:
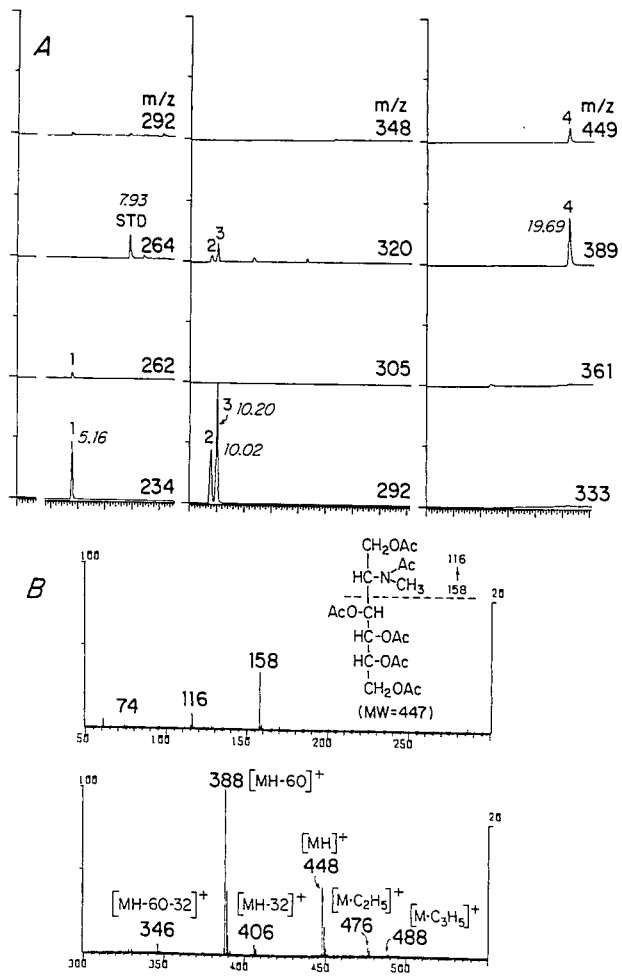
FIG. 3 shows a selected ion chromatogram of partially O-methylated (monodeuterio) aditol and hexosaminitol acetates from the hydrosate of permethylated disialosyl Le$^a$ (panel A) and the mass spectrum of a synthetic derivative (panel B)

Referring to FIG. 3, Panel A is a selected ion chromatogram of partially O-methylated (monodeuterio) aditol and hexosaminitol acetates from the hydrolysate of permethylated disialosyl Le$^a$. Derivatives were separated on a DB-5 capillary column temperature-programmed from 140° to 250° at 4° C./min. Splitless injection was used, with splitter closed and oven temperature 50° C. for 40 seconds following injection, after which time the splitter was opened and the oven temperature raised to the program starting point (taking 110 seconds more). Derivatives were identified by methane (300 μ) chemical ionization mass spectrometry with selected ion monitoring (cycle time, 1 sec), using a Finnigan 3300 gas chromatograph/mass spectrometer adapted for use with fused silica capillary columns and 6110 data system. The ordinate indicates relative intensity of each ion at mass number indicated. The abscissa indicates retention time; the italicized numbers are retention times in minutes, measured from the point at which the splitter is opened. Peaks identified were: (STD), 2,3,4,6-tetra-O-Me-Glc added as retention time standard; (1), 2,3,4-tri-O-Me-Fuc; (2), 2,3,6-tri-OMe-Gal; (3), 2,4,6-tri-O-Me-Glc; and (4), per-O-acetyl-GlcNacMe. No other sugar peaks were detected. Identifications were made on the basis of appropriate MH⁺, (MH-32)⁺, and (MH-60)⁺ ions and retention indices compared with authentic standards, and confirmed in the case of (4) by co-injection with a synthetic derivative as described below.

Preparation of 1,3,4,5,6-penta-O-acetyl-2-N-methylacetamido-2-deoxyglucitol

During the course of methylation analysis, we expected the yield of fully-substituted GlcNAcME. Since such a compound had not been analyzed previously, a reference compound was prepared. D-glucosamine was N-methylated according to the method of Kuehl et al. (J.Am.Chem.Soc. 69:3032–3035, 1947) as modified by Tai et al. (J.Biochem. 78:679–686, 1975). The product was acetylated as described (J.Am.Chem.Soc. 69:3032–3035, 1947) and then subjected to the hydrolysis-reduction-acetylation sequence as described previously for permethylated glycolipids (J.Biol.Chem. 259:14773–14777, 1984), using NaBH₄ rather than NaBD₄ for reduction. The resulting product, 1,3,4,5,6-penta-O-acetyl-2-N-methylacetamido-2-deoxyglucitol, analyzed by GC-CI-MS as above, had the expected molecular weight (MH⁺=448 amu) and fragmentation, and had a retention time later than any of the mono-O-methyl-GlcNAcMe derivatives previously described (J.Am.Chem.Soc. 69:3032–3035, 1947; Arch.Biochem.-Biophys. 155:464–472, 1973).

Panel B of FIG. 3 shows the mass spectrum of per-O-acetyl-GlcNAcMe (1,3,4,5,6-penta-O-acetyl-2N-methylacetamido-2-deoxyglucitol). The spectrum of this synthetic derivative was obtained under conditions identical to those used for the GC-MS analysis above, except that the mass range 60–500 a.m.u. was scanned (cycle time 2.2 sec) by the data system. When a sample of this material was co-injected with the sample analyzed above, and analyzed by selected ion monitoring-methane CI, the peaks for m/z 448 and 388 for MH⁺and (MH-60)⁺for the standard coincided exactly with those at m/z 449 and 389 for the hydrolysate obtained from disialosyl Le$^a$. The derivative shown in peak 4 of FIG. 3A was identified as GlcNAcMe-1,3,4,5,6-penta-O-acetate (1,3,4,5,6-penta-O-acetyl-2-N-methylacetamido-2-deoxyglucitol) on comparison of the spectra with those of the synthetic derivative.

In a separate analysis, the methylated ganglioside fraction gave only 4,7,8,9-tetra-O-Me-NeuAcMe but did not give any trace quantity of 4,7,9-tri-O-Me-NeuAcMe (data not shown). Thus, sialic acids cannot be linked through NeuAcα2→8NeuAc structure, but are independently linked to the terminal Gal and internal GlcNAc through 2→3 and 2→6 linkages, respectively.

Enzymatic degradation

In order to obtain further structural information, lipds were hydrolyzed by two kinds of sialidases, *Clostridium perfringense* and *Arthrobacter ureafaciens*(both purchased from Sigma Chemical Co., St. Louis, MO), in the presence or absence of sodium deoxytaurocholate. Sialiase of *Arthrobacter ureafaciens* showed broader and less restricted specificity than *Clostridium perfringense* sialidase (J.Biol.Chem. 254:7845–7854, 1979). Arthrobacter sialidase can hydrolyze sialosyl 2→6 GlcNac linkage in the absence of detergent (J.Biol.Chem. 254:8548–8553, 1979), while Clostridium sialidase cannot hydrolyze the same linkage in the absence of detergent. 10 μg of glycolipid in chloroform-methanol (2:1) were mixed with 20 μg of sodium deoxytaurocholate in chloroform-methanol. The solution was evaporated under nitrogen stream and the residue was dissolved in 20 μl of 0.1 M sodium acetate, pH 4.5, by sonication. To this mixture, 20 μl of either the Clostridium or the Arthrobacter sialidase were added. Each enzyme preparation contained 5 units/ml. The mixture was incubated at 37° C. for 18 hours. In a separate experiment, 10 μg of glycolipid was dissolved in 20 μof sodium acetate buffer as above and hydrolyzed under the same conditions.

The hydrolysates were diluted with water, passed through a column of "Bond-Elut C18" (Analytichem International, Harbor City, CA) washed with 5 column volumes of water, and glycolipds were subsequently eluted with 5 column volumes of chloroform-methanol (2:1, v/v). Degradation products were identified by HPTLC followed by immunostaining with monoclonal antibodies as described below.

Monoclonal antibody reagents used and immunostaining of intact and sialidase-degraded glycolipids.

The monoclonal antibody FH7 directed to disialosyl Le$^a$ was prepared as described in Example 3. Anti-Le$^a$ antibody, designated CF4C4, was donated by Dr. W. W. Young (Dept. of Pathology, University of Virginia Medical Center, Charlottesville, VA). The CF4C4 antibody defines the Le$^a$ structure (Gal$\beta$1→3[Fuc$\alpha$1→4]GlcNAc$\beta$1→R), but is not reactive with partial structures such as Fuc$\alpha$1→4GlcNAc or Gal$\beta$1→3GlcNAc, nor with its positional isomer Le$^x$ (J.Biol.Chem. 258:4890–4894, 1983). The monoclonal antibody FH6, which defines sialosyl Le$^x$ carried by a long type 2 chain structure (NeuAc$\alpha$2→3Gal$\beta$1→4[Fuc$\alpha$1→3]glcNAc$\beta$1→3Gal$\beta$1→4GlcNAc$\beta$1→3Gal$\beta$1→R), was established as described in J.Biol.Chem. 259:10511–10517, 1984. The monoclonal antibody N-19-9 (Somatic Cell Genetics 5:957–972, 1979), which defines sialosyl Le$^a$ structure (NeuAc$\alpha$1→3Gal$\beta$1→3-[Fuc$\alpha$1→4]GlcNAc$\beta$1→R) (Science 212:55–56, 1981), was donated by Dr. Koprowski (Wistar Institute, Philadelphia, PA). The specificity of the N-19-9 antibody has been well-characterized by Magnani et al. (J.Biol.-Chem. 257:14365–14369, 1982). Another monoclonal antibody directed to sialosyl Le$^a$ structure, designated CSLEA-1, was provided by Dr. Paul Teraskai (Dept. of Surgery, UCLA School of Medicine, Los Angeles, CA). The specificity of the CSLEA-1 antibody was recently characterized (Cancer Res. 45:435–437, 1985). The monoclonal antibody 1B9, which defines NeuAc$\alpha$2→6Gal$\beta$1→4GlcNAc$\beta$1→R structure, was established as described in J.Biol.Chem. 254:8223–8229, 1979; J.Biol.Chem. 258:11819–11822, 1983. The 1B2 antibody, which defines type 2 chain (J.Biol.Chem. 256:10967–10972, 1981), and various antibodies (FH1, FH2, FH3) that define X (Le$^x$) determinant carried by various lengths of type 2 chain were also established as previously described (J.Biol.Chem. 259:4681–4685, 1984).

Glycolipids and their enzyme degradation products were separated on "Bond-Elut C18" column (Analytichem International, Harbor City, CA) as described in J.Biol.Chem. 257:14365–14369, 1982, and were further separated into components by preparative HPTLC (Baker's plate, J. T. Baker Chemical Co., Phillipsburg, NJ) extracted with isopropanol-hexane-water (55:20:25, v/v/v) as above. Immunostaining was performed by a modified procedure (J.Biol.Chem. 257:14865–14874, 1982) of Magnani et al. (Anal.Biochem. 109:399–402, 1980).

Determination of the Enzyme-Degraded Products

Figure 4:
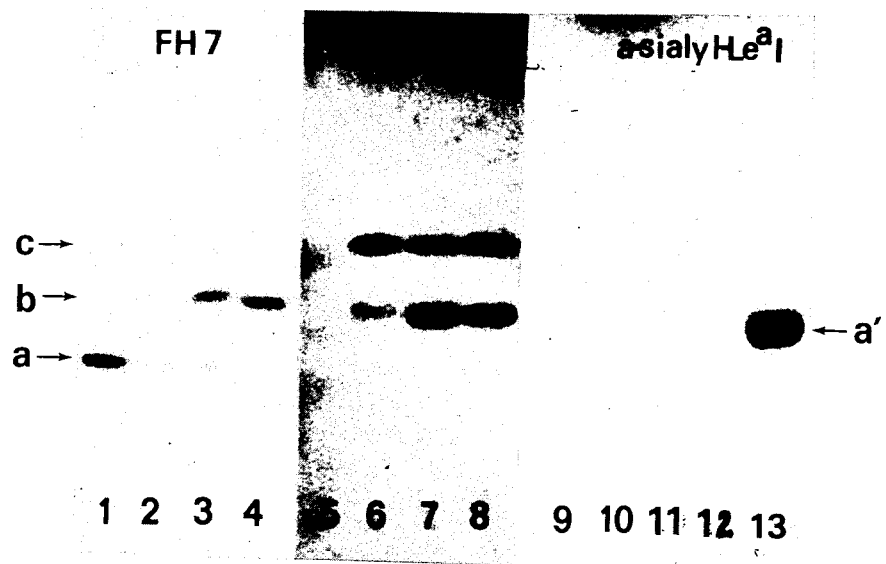
FIG. 4 shows hydrolysis products of disialosyl Le$^a$ with sialidases from *Clostridium perfringense* and *Arthrobacter ureafaciens*.
Figure 5:
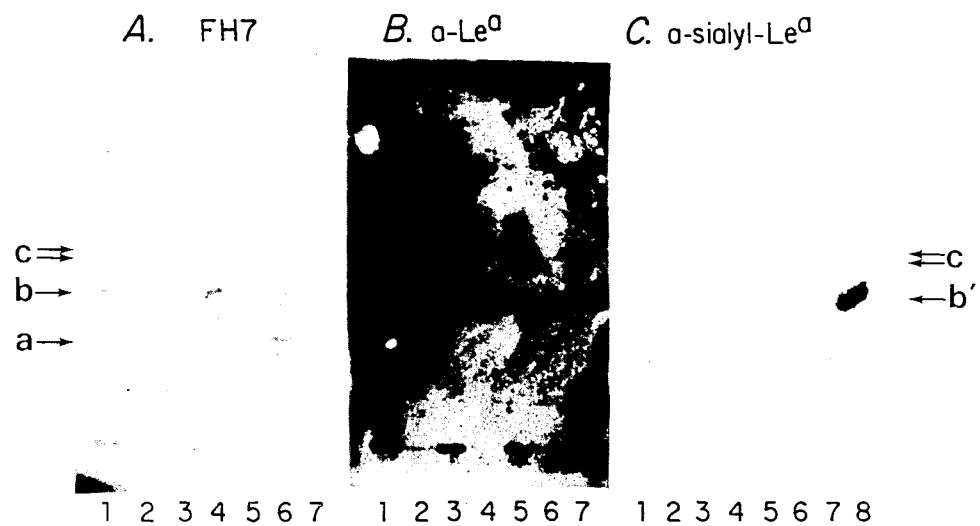
FIG. 5 shows thin-layer chromatographic immunostaining of the sialidase hydrolysis products of disialosyl Le$^a$ and further degradation of intermediate products by acetic acid hydrolysis; and, FIG. 6 is a chart comparing the levels of FH7-defined disialosyl Le$^a$ antigen in sera of patients with colonic cancer before and after surgical removal of the cancer.

Treatment of the disialosyl Le$^a$ antigen with *Clostridium perfringense* sialidase in the absence of detergent preferentially hydrolyzed the sialosyl 2→3 linkage to Gal, and converted the antigen into an intermediate product that reacts with both FH7 and anti-Le$^a$ antibody (FIG. 4, spot b in lanes 3, 4, 7, and 8). Hydrolysis of disialosyl Le$^a$ antigen with *Arthrobacter ureafaciens* sialidase, which is capable of hydrolyzing both the sialosyl $\alpha$2→3 linkage to Gal and the sialosyl $\alpha$2→6 linkage to GlcNAc even in the absence of detergent, converted the disialosyl Le$^a$ antigen into Le$^a$ antigen having the same HPTLC mobility as a ceramide pentasaccharide, whereby the quantity of the intermediate product (spot b) decreased greatly (FIG. 4, lanes 2 and 6). The intermediate spot b isolated by HPTLC had the same mobility as monosialosyl Le$^a$I (IV$^3$NeuAcIII$^4$-FucLc$_4$; see structure B, TABLE 1; J.Biol.Chem. 257:14365–14369, 1982) and reacted with FH7 and anti-Le$^a$ antibodies (FIG. 5, panels A and B, lane 4) but not with anti-sialosyl Le$^a$ N-19-9 or CSLEA-1 antibodies (FIG. 5, panel C). This intermediate product was converted to Le$^a$ antigen by treatment with 1% acetic acid at 100° C. for 1 hour (FIG. 5, panel A, lane 5) and by incubation with Arthrobacter sialidase in the absence of detergent (data not shown).

FIG. 4 shows hydrolysis products of disialosyl Le$^a$ with sialidases from *Clostridium perfringense* and *Arthrobacter ureafaciens*. Lanes 1, 5 and 9 are purified intact disialosyl Le$^a$ antigen. Lanes 2, 6 and 10 are purified disialosyl Le$^a$ antigen treated with Arthrobacter sialidase in the absence of detergent. Lanes 3, 7 and 11 are purified disialosyl Le$^a$ antigen treated with Clostridium sialidase in the absence of detergent. Lanes 4, 8 and 12 are purified disialosyl Le$^a$ antigen treated with *Clostridium perfringense* in the presence of detergent. Lane 13 is monosialosyl Le$^a$I isolated from colonic cancer tissue. Lanes 1–4 were stained by FH7; lanes 5–8 were stained by anti-Le$^a$ antibody CF4C4 (J.Biol.Chem. 258:4890–4894, 1983); and lanes 9–12 were stained by anti-sialosyl Le$^a$I (CSLEA-1).

FIG. 5 shows TLC immunostaining of the sialidase hydrolysis products and further degradation of an intermediate product by acetic acid hydrolysis. Disialosyl Le$^a$ antigen was hydrolyzed by *Clostridium perfringense* sialidase in acetate buffer, pH 5.0, without addition of detergent. Three cleavage products (represented by bands a, b, and c) were purified and separated into bands as described above. Lane 1, hydrolysate before separation containing three bands. Lane 2, the purified fast-migrating band (band c). Lane 3, the fast-migrating band treated with acetic acid. Lane 4, the purified intermediate hydrolysis product (band b). Lane 5, the intermediate band treated with acetic acid. Lane 6, intact disialosyl Le$^a$ treated sialic acid. Monosialosyl Le$^a$ antigen (IV$^3$NeuAcIII$^4$FuLc$_4$) is seen in lane 8. Panel A was stained by antibody FH7. Panel B was stained by anti-Le$^a$ antibody CF4C4. Panel C was stained by anti-sialosyl Le$^a$I (CSLEA-1).

EXAMPLE 3

Preparation of a Monoclonal Antibody Directed to Disialosyl LE$^a$

The disialoganglioside fraction of colonic adenocarcinoma from Example 1, coated on acid-treated *Salmonella minnesota*, was used as immunogen according to the method described in J.Biol.Chem. 257:12752, 1982, hereby incorporated by reference. Specifically, the disialoganglioside fraction purified by preparative HPTLC developed in a solvent mixture of chloroform-methanol-water (60:40:9, v/v/v containing 0.02% CaCl$_2$) was separated as a single band that still contained disialosylgalactosyl globoside; (the ratio of disialosyl Le$^a$ to disialosylgalactosyl globoside in the preparation used as immunogen was about 1:2). About 5 μg of the ganglioside fraction was mixed with 20 μg of *Salmonella minnesota* and injected intravenously into BALB/c mice on Day 0, and 2 μg of the ganglioside fraction mixed with 20 μg of *Salmonella minnesota* was injected every four days, totaling seven intravenous injections. On the fourth day after the last injection, spleen cells were harvested and fused with SP-2 mouse myeloma cells. Hybridomas were cloned on 96-well plates (Dynatech Immunolon plate, Dynatech Laboratories, Alexandria, VA) coated with purified disialosyl Le$^a$ glycolipid (10 ng/well), cholesterol (30 ng/well), and lecithin (50 ng/well). Cloning was performed repeatedly.

The hybridoma secreting the antibody designated FH7 was selected, and the specificity of the antibody FH7 was characterized, as described in Examples 4, 5 and 6.

EXAMPLE 4
Determination of the Antibody Specificity

The hybridoma secreting the FH7 antibody was selected by positive reaction with disialosyl Le$^a$ ganglioside and negative reaction with other disialosyl and monosialosyl gangliosides having closely related structures.

TABLE 1 shows the structures of several fucogangliosides used in this assay. The disialo Le$^a$ ganglioside (IV$^3$NeuAcIII$^6$NeuAcIII$^4$FucLc$_4$) and monosialo Le$^a$II, structures A and C, were prepared as in Example 1. Structure B is monosialosyl Le$^a$I (IV$^3$NeuAcIII$^4$FucLc$_4$), purified from the monosialoganglioside fraction of human colonic adenocarcinoma tissue by HPTLC in an isopropanol-hexane-water system followed by preparative HPTLC as described in J.Biol.Chem. 257:14365, 1982. Structure D is the Le$^a$ antigen (III$^4$FucLc$_4$), prepared either (i) by extensive hydrolysis of disialo Le$^a$ with *Clostridium perfringense* or *Arthrobacter ureafaciense* sialidase in the presence of detergent, or (ii) by treating the monosialo Le$^a$II antigen with 1% acetic acid at 100° C. Structure E is disialosyllactotetraosylceramide (IV$^3$NeuAcIII$^6$NeuAcLc$_4$), isolated as described in Example 1. Other fucogangliosides used in this assay include the following: monosialosyl Le$^x$ (IV$^3$-NeuAcIII$^3$FucnLc$_4$), monosialosyl 2→3 lactoneotetraosylceramide (IV$^3$NeuAcnLc$_4$), monosialosyl 2→6 lactoneotetraosylceramide (IV$^6$NeuAcnLc$_4$), and disialosyllactoneotetraosylceramide (IV$^3$NeuAca2→8NeuAcnLc$_4$). Monosialosyl Le$^x$ was prepared from human kidney as described in J.Biol.Chem. 251:7517, 1976. The monosialosyl 2→3 lactoneotetraosylceramide and monosialosyl 2→6 laconeotetraosylceramide were prepared from colonic adenocarcinoma tissue as described in J.Biol.Chem. 258:11818, 1983. The disialosyllactoneotetraosylceramide was isolated as described in Example 1.

The aforesaid glycolipids separated on thin layer chromatography were immunostained acording to a modified procedure (J.Biol.Chem. 257:14865–14874, 1982) of Magnani et al. (Anal.Biochem. 109:399–402, 1980). A mini-HPTLC plate was used in order to minimize the amounts of glycolipid and antibody. A Baker HPTLC plate (J. T. Baker Chemical Co.) was cut into 5×6 cm pieces by a glass cutter. Glycolipid samples (about 0.2–0.3 μg) were applied on duplicate plates by needle syringe (Hamilton Co., Reno, NV) on a baseline within 3–4 mm. Glycolipid bands were dissolved in solvent of chloroform/methanol/water (50:40:10) containing 0.2% CaCl$_2$. Spots on control chromatograms were detected by 0.2% orcinol in 2N sulfuric acid. Duplicate plates were immunostained with the antibody FH7 or with antibodies N-19-9, CSLEA-1, or C4-11. The antibody N-19-9 and the anitbody CSLEA-1 react with monosialosyl Le$^a$ antigen, the major tumor-associated type 1 chain antigen present in various gastrointestinal tumors. The antibody C4-11 reacts with the Le$^a$ antigen.

The results of these immunostaining assays are summarized in TABLE 1. The antibody FH7 is highly specific to the disialo Le$^a$ structure and does not cross-react with monosialosyl Le$^a$I (structure B, TABLE 1), disialosyllactoneotetraosylceramide, disialosyllactotetraodylceramide (structure E, TABLE 1), and many other disialosyl and monosialosyl gangliosides. The antibody FH7 reacts, however, with an intermediate degradation product (monosialosyl Le$^a$II; structure C, TABLE 1), which indicates that the antibody FH7 recognizes a fully-substituted GlcNAc structure with $\beta1\rightarrow3$ galactosyl, $\alpha1\rightarrow4$ fucosoyl, and $\alpha2\rightarrow6$ sialosyl as shown below:

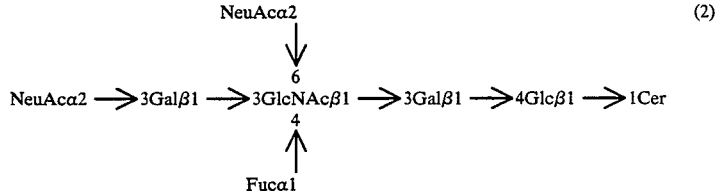

(2)

In contrast, the antibodies N-19-9 and CSLEA-1 did not react with either disialo Le$^a$ or monosialo Le$^a$II. Antibody C4-11 reacted with monosialo Le$^a$II, as expected, but did not react with disialo Le$^a$.

EXAMPLE 5
Reactivity of Various Gangliosides with the Monoclonal Antibody FH7

The specificity of the monoclonal antibody FH7 was also determined by solid-phase radioimmunoassay was performed on vinyl strips (Costar Laboratories, Cambridge, MA) according to the procedure described in Cancer Res. 43:4997–5005, 1983. Reactivities with antibody dilution were determined with 10 ng of ganglioside, 50 ng of lecithin, and 30 ng of cholestrol coated per well; the original antibody dilution, the original well contained 100 ng of ganglioside, 500 ng of lecithin, and 300 ng of cholesterol; the antibody concentration applied to each well was 150 times diluted FH7 supernatant.

Positive reactivity with disialosyl Le$^a$ (IV$^3$-NeuAcIII$^4$FucIII$^6$NeuAcLc$_4$) were observed. A weak reactivity with disialosyllactotetraosylceramide (IV$^3$-NeuAcIII$^6$NeuAcLc$_4$) was due to the presence of the cross-reacting intermediate degradation product monosialyl Le$^a$II. In contrast, negative reactivity was observed for FH7 with monosialosyl Le$^a$I (IV$^3$-NeuAcIII$^4$FucLc$_4$), sialosyl Le$^x$ (IV$^3$NeuAcIII$^3$-FucnLc$_4$), sialosyl 2→3 lactoneotetraosylceramide (IV$^3$NeuAcnLc$_4$), disialosyllactoneotetraosylceramide (IV$^3$NeuAc2→8NeuAcnLc$_4$), and sialosyl 2→6 lactoneotetraosylceramide (IV$^6$NeuAcnLc$_4$).

EXAMPLE 6

Reactivity of FH7 with Disialostk LE$^a$ Before and after Soalidase Treatment

The antigen defined by the antibody FH7 was identified as disialosyl Le$^a$ (Table I, structure A) based on the following observations: (i) the chromatographic behavior of the antigen on DEAE-Sepharose coincides with that of a disialoganglioside (eluted with 0.13–0.15 M ammonium acetate in methanol); (ii) treatment of the antigen with *Clostridium perfringense* sialidase in the absence of detergent preferentially hydrolyzed sialosy 2→3 Gal residue to convert the antgen into monosialosyl Le$^a$II (Table 1, structure C), an intermediate product that reacts with both FH7 and the Le$^a$ antibody CF4C4; (iii) extensive hydrolysis with *Clostridium perfringense Arthrobacter ureafaciense* sialidase in the presence of detergent caused the disappearance of the intermediate monosialosyl Le$^a$II and resulted in the appearance of Le$^a$ antigen, which is reactive to the anti-Le$^a$ antibody CF4C4 but does not react with the antibody FH7; (iv) the purified intermediate was converted to Le$^a$ antigen by treatment with 1% acetic acid at 100° C. (data not shown); and (v) methylation analysis did not detect NeuAc2→8NeuAc structure, but did detect terminal Fuc, 3→substituted Gal, and 3,4,6-substituted GlcNac (i.e., non-methylated GlcNacMe).

EXAMPLE 7

Determination of Immunoglobulin Subclass

The immunoglobulin subclass of the antibody FH7 was determined with subclass-specific antibodies purchased from Cappel Laboratories (Cochranville, PA). FH7 is an IgG3 antibody.

EXAMPLE 8

Reactivities of Antibodies FH7 and FH6 with Various Human Tumor Cell Lines

The antibody FH7 exhibited a more restricted reactivity with various human tumor cell lines than did the FH6 antibody. The FH6 antibody is directed to monosialosyl dimeric Le$^x$ (VI$^3$NeuAcV$^3$III$^3$Fuc$_2$nLc$_6$) which accumulates in human colonic adenocarcinoma but is absent in normal colonic mucosa. J.Biol.Chem. 259(16):10511–10517, 1984.

The assayed human tumor cell lines included gastric cancer cells, lung cancer cells, ovarian adenocarcinoma, B cell lines, human fibroblasts, human teratocarcinoma, and human cervical carcinoma. Cells were fixed on polylysine-coated Linbro plates (Flow Laboratories, McLean, VA) by treating with glutaraldehyde, and antibody binding was determined as described in J.Biol.Chem. 259(7):4681–4685, 1984.

EXAMPLE 9

Reactivity of FH7 with Various Normal Cells

The antibody FH7 did not detect any antigen in the ganglioside fraction isolated from six cases of normal colon, five cases of normal liver, two cases of normal lung, and three samples of whole normal blood cell membranes. The fact that the FH7 antibody reacts with a single disialoganglioside present in the extracts from colonic and gastric adenocarcinoma yet does not react with any gangliosides in extracts of normal colonic mucosa, normal liver, normal lung, and normal blood cell membranes indicates a close association of FH7-defined antigen expression with human malignancy.

EXAMPLE 10

Determination of Antigen Level in Serum

The antigen level in serum was determined by inhibition of antibody FH7 binding to glycolipid antigen coated on a vinyl surface (Costar, Cambridge, MA) with cholesterol and lecithin. In order to minimize non-specific inhibition caused by serum, an unknown component present in serum was eliminated by precipitation at pH 5.0±0.1. The steps of this determination were as follows: (i) Equal volumes of serum and 0.05 M sodium citrate buffer, pH 3.77, were mixed together (pH of the mixture became 5.0±0.1); a cloudy precipitate was eliminated by centrifugation at 2,000 rpm for 10 min. (ii) 50$\mu$l of the supernatant of the acidified serum was placed in wells A, B, and C, and 50$\mu$l of buffer solution of equal strength and composition was placed in wells D and E. (iii) To wells A, B, and D was added the antibody FH7 (50$\mu$l of 40 times diluted culture supernatant with 0.05 M of citrate buffer, pH 5.0), and to wells C and E was addded 50$\mu$l of the same buffer solution (0.05 M citrate buffer, pH 5.0). (iv) After incubation at 4° C. overnight, 50$\mu$l of the incubation mixture from each well (A-E) was transferred to another well (A'-E') that was coated with disialoganglioside (10 ng) of colonic cancer with 30 ng of cholesterol and 50 ng of egg lecithin. (v) After standing at room temperature for two hours, each well was washed with PBS three times and incubated with $^{125}$I-labeled protein A (8×10$^4$ cpm/well) for one hour. (vi) Each well was washed with PBS three times and counted in a gamma counter. The percentage of inhibition was calculated as follows: 100-[(Ct-Cb)/(Cp-Cd)]×100; Ct, count with the complete system, i.e., in the presence of serum and antibody (mean count of wells A' and B'); Cb, count in the presence of serum without antibody (well C'); Cp, count with serum, i.e., in the presence of antibody and buffer (well D'); Cd, count without serum and antibody (background count; well E').

EXAMPLE 11

Antibody FH7 Defined Antigen Level in Sera of Patients with Cancer.

The levels of FH7-defined antigen in sera of normal subjects, patients with non-malignant diseases, and patients with malignancy were determined as described in EXAMPLE 10. Sera of all normal subjects showed less than 60% inhibition, and many of them (46%) showed inhibition. A similar low degree of inhibition was demonstrated in sera of patients with non-malignant diseases. Essentially all sera of patients with non-inflammatory, non-malignant diseases showed less than 60% inhibition, and only 20% of sera of all patients with chronic inflammatory diseases showed more than 60% inhibition. In contrast, the serum FH7-directed antigen level was significantly higher in many types of human cancer, particularly colonic, gastric, pancreatic, and bladder cancer. Sera of only 2 out of 44 cases of malignancy showed less than 30% inhibition. Sera of all other cases of malignancy showed higher than 30% inhibition, and as many as 58% of milignant cases showed more than 60% inhibition. Furthermore, some relatively early cases of bladder cancer (stages I–II), gastric cancer (stages I–II), and colonic cancer (stages II–III) showed a high degree of inhibition and FH7 antibody binding.

EXAMPLE 12

Pre-and Postoperative Serum Levels of FH7-Defined Antigen

Figure 6:
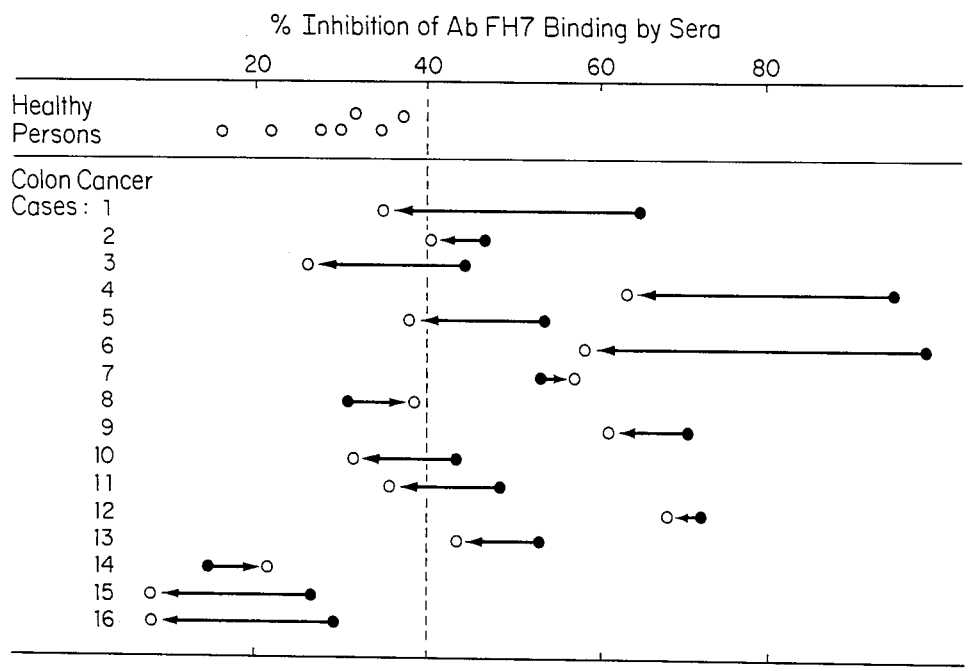

The FH7-defined antigen levels in sera of patients with colonic cancer were compared before and afterr surgical removal of the colonic cancer. The results are shown in FIG. 6. Class 1–12 are stage II–III, and cases 13–16 are stages I–II. Solid and open circles respectively represent FH7-defined disialo Le$^a$ antigen levels in patient sera before and after surgery. In a large number of cases the antigen level decreased after removal of cancer, although a few cases did not show significant changes or even showed a slight reverse effect. Interestingly, a few cases were observed that showed a low antigen level in colonic cancer, yet the antigen level decreased after removal of tumor by surgical operation.

In contrast, the serum antigen levels of both monosialosyl Le$^a$ and monosialosyl Le$^x$ reportedly became elevated in patients only at stages III or IV. Cancer Res. 45:435, 1985; Quentmeier, A., et al., Carbohydrate antigen 19-9 and carcinoembryonic antigen in gastric cancer detection, staging, and follow up, in Abstract Book: Advances in Cancer Research (Abstract 21), Processings of the XI Annual Meeting, Stockholm, Sweden, Sept. 11 to 15, 1983. Therefore, the disialosyl Le$^a$ antigen defined by the antibody FH7 is distinctively useful for diagnosing early stage human cancer using serum samples.

It is contemplated that radiolabeled antibody FH7 will also be particularly useful for imaging tumor location in vivo. For example, a radionuclide such as I-123 can be coupled to the antibody FH7 using standard methodologies, such as those employing the Bolton-Hunter reagent. The radiolabeled antibody can be admixed in a suitable carrier solution and introduced, e.g., intravenously or rectally, into the body of a mammal. The body can thereafter be scanned with a scintillation detector such as a gamma camera to localize tumor tissue bearing antigen reactive with the radiolabeled antibody FH7.

The antibody FH7 is also suitable for implementing cancer immunological therapy. The antibody FH7 can be coupled to a radionuclide or antitumor drug and introduced, such as by intravenous injection, into the body of a mammal in order to differentially deliver the radionuclide of drug to tumor tissues bearing antigen reactive with the FH7 antibody. Furthermore, in view of the recent application of IgG3 antibody directed to a glycolipid antigen that supresses tumor growth in vivo (Proc.Natl.Acad.Sci. USA 82:1242-1246, 1985), the IgG3 antibody FH7 is considered to be a very good candidate for immunotherapy via direct intravenous injection of unconjugated antibody.

While the present invention has been described in conjunction with preferred embodiments, one of ordinary skill after reading the foregoing specification will be able to effect various changes, substitutions of equivalents, and alterations to the compositions and methods set forth herein. It is therefore intended that the protection granted by Letters Patent hereon be limited only by the definitions contained in the appended claims and equivalents thereof.

The embodiments of the invention in which an exclusive property or privilege is claimed are defined as follows:

1. A monoclonal antibody capable of specifically binding to the fucoganglioside disialosyl Le$^a$ (IV$^3$-NeuAcIII$^6$NeuAcIII$^4$FucLc$_4$).

2. A diagnostic test kit for assaying the presence of disialosyl Le$^a$ comprising the monoclonal antibody of claim 1 in combination with means for detecting the binding of said antibody to disialosy Le$^a$.

3. A monoclonal antibody capable of specifically binding to the fucoganglioside monosialosyl Le$^a$II (III$^6$-NeuAcIII$^4$FucLc$_4$).

4. A diagnostic test kit for assaying the presence of disialosyl Le$^a$ comprising the monoclonal antibody of claim 3 in combination with means for detecting the binding of said antibody to disialosyl Le$^a$.

5. A hybridoma cell line capable of producing a monoclonal antibody capable of specifivcally binding with fucogangliosides selected from the group consisting of disialosyl Le$^a$ (IV$^3$NeuAcII$^6$NeuAcIII$^4$FucLc$_4$) and monosialosyl Le$^a$II (III$^6$NeuAcIII$^4$FucLc$_4$) but not specifically binding with any of IV$^3$NeuAcIII$^4$FucLc$_4$, IV$^3$NeuAcnLc$_4$, IV$^6$NeuAcnLc$_4$, or IV$^3$NeuAcα2→8NeuAcnLc$_4$.

6. Hybridoma cell line ATCC No. HB 8861 according to claim 5.

7. A monoclonal antibody produced by the hybridoma cell line of claim 5.

8. An IgG3 antibody produced by the hybridoma cell line of claim 5.

9. The monoclonal antibody of claim 7 coupled to a radionuclide.

10. The monoclonal antibody of claim 7 coupled to an antitumor drug.

11. The monoclonal antibody of claim 7 coupled to a detectable marker.

12. The monoclonal antibody of claim 11 wherein the detectable marker is selected from the group consisting of enzymes, chromophores, fluorophores, coenzymes, chemiluminescent materials, enzyme inhibitors, paramagnetic metals, and radionuclides.

13. A diagnostic test kit for assaying the presence of disialosyl Le$^a$ comprising the monoclonal antibody of claim 7 in combination with means for detecting the binding of said antibody to disialosyl Le$^a$.

* * * * *

UNITED STATES PATENT AND TRADEMARK OFFICE
CERTIFICATE OF CORRECTION

PATENT NO. : 4,851,511
DATED : July 25, 1989
INVENTOR(S) : Hakomori et al.

It is certified that error appears in the above-identified patent and that said Letters Patent is hereby corrected as shown below:

Column 1, lines 51-59 (Equation 1):

"
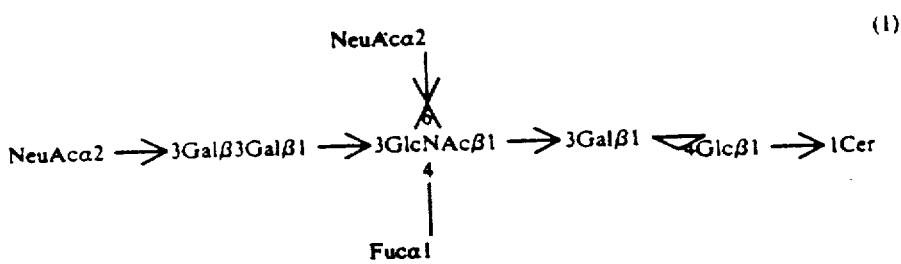
"

should be

--
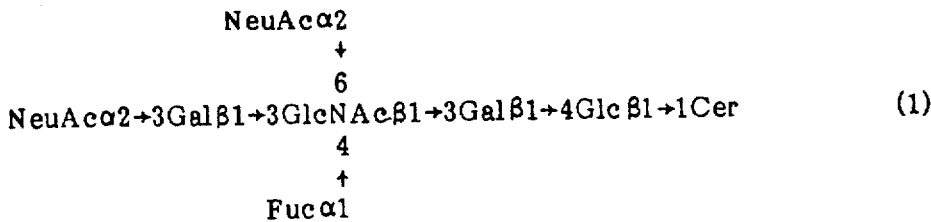
--

Column 3, between lines 13 and 14, insert the following paragraph:
--The representative antibody FH7 is produced by hybridoma cell line ATCC No. HB 8861, which was deposited on July 9, 1985, at the American Type Culture Collection, 12301 Parklawn Drive, Rockville, MD 20852.--

UNITED STATES PATENT AND TRADEMARK OFFICE
CERTIFICATE OF CORRECTION

PATENT NO. : 4,851,511

DATED : July 25, 1989

INVENTOR(S) : Hakomori et al.

It is certified that error appears in the above-identified patent and that said Letters Patent is hereby corrected as shown below:

Column 2, line 28: "malignacy" should be --malignancy--

Columns 3 and 4, lines 40-68 and 1-18 (TABLE 1):

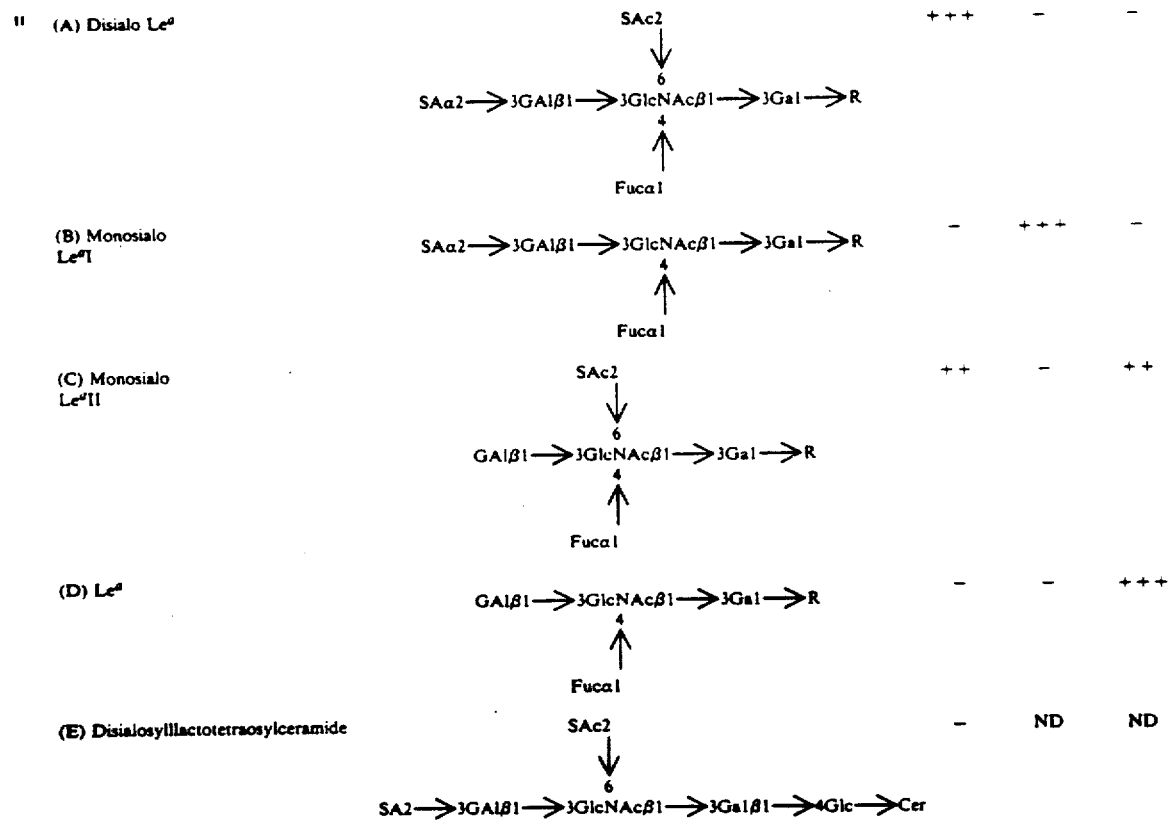

UNITED STATES PATENT AND TRADEMARK OFFICE
CERTIFICATE OF CORRECTION

PATENT NO. : 4,851,511
DATED : July 25, 1989
INVENTOR(S) : Hakomori et al.

Page 3 of 7

It is certified that error appears in the above-identified patent and that said Letters Patent is hereby corrected as shown below:

should be

-- 
A) Disialo Le$^a$ $$SA\alpha 2$$
$$\downarrow$$
$$6$$
$$SA\alpha 2 \rightarrow 3Gal\beta 1 \rightarrow 3GlcNAc\beta 1 \rightarrow 3Gal \rightarrow R$$
$$4$$
$$\uparrow$$
$$Fuc\alpha 1$$

+++    -    -

B) Monosialo Le$^a$I $$SA\alpha 2 \rightarrow 3Gal\beta 1 \rightarrow 3GlcNAc\beta 1 \rightarrow 3Gal \rightarrow R$$
$$4$$
$$\uparrow$$
$$Fuc\alpha 1$$

-    +++    -

C) Monosialo Le$^a$II $$SA\alpha 2$$
$$\downarrow$$
$$6$$
$$Gal\beta 1 \rightarrow 3GlcNAc\beta 1 \rightarrow 3Gal \rightarrow R$$
$$4$$
$$\uparrow$$
$$Fuc\alpha 1$$

++    -    ++

D) Le$^a$ $$Gal\beta 1 \rightarrow 3GlcNAc\beta 1 \rightarrow 3Gal \rightarrow R$$
$$4$$
$$\uparrow$$
$$Fuc\alpha 1$$

-    -    +++

E) Disialosyll-lactotetraosyl-ceramide $$SA\alpha 2$$
$$\downarrow$$
$$6$$
$$SA2 \rightarrow 3Gal\beta 1 \rightarrow 3GlcNAc\beta 1 \rightarrow 3Gal\beta 1 \rightarrow 4Glc \rightarrow Cer$$

-    ND    ND

--

UNITED STATES PATENT AND TRADEMARK OFFICE
CERTIFICATE OF CORRECTION

PATENT NO. : 4,851,511
DATED : July 25, 1989
INVENTOR(S) : Hakomori et al.

It is certified that error appears in the above-identified patent and that said Letters Patent is hereby corrected as shown below:

Column 5, line 14 (TABLE 1): "Disialosylllactotetraosylceramide" should be --Disialosyllactotetraosylceramide--

Column 5, line 47: "Arthrobacter" should be --<u>Arthrobacter</u>--

Column 7, line 10: "FulcLc$_4$" should be --FucLc$_4$--

Column 7, line 53: "(VI$^3$NeuAcIII$^4$FucLc$_4$;" should be --IV$^3$NeuAcIII$^4$FucLc$_4$;--

Column 9, line 37: "Lipds" should be --Lipids--

Column 10, line 63: "(IV$^3$NeuAcnLc$_4$);" should be --(IV$^3$NeuAcnLc$_4$)$^3$;--

Column 11, lines 1-2: after "ganglioside" delete "(VI$^3$NeuAcV$^3$FucIII$^3$FucnLc$_6$) and 6C ganglioside"

Column 11, line 5: "(VI$^3$" should be --(IV$^3$--

Column 11, line 53: "2,3,4,6-tetra-O-Me-Glc" should be --2,3,4,6-tetra-<u>O</u>-Me-Glc--

Column 11, line 54: "2,3,4-tri-O-Me-Fuc" should be --2,3,4-tri-<u>O</u>-Me-Fuc--

Column 11, lines 54-55: "2,3,6-tri-OMe-Gal" should be --2,3,6-tri-<u>O</u>Me-Glc--

Column 11, line 55: "2,4,6-tri-O-Me-Glc" should be --2,4,6-tri-<u>O</u>-Me-Gal--

Column 11, lines 55-56: "per-O-acetyl-GlcNacMe" should be --per-<u>O</u>-acetyl-GlcNacMe--

Column 12, line 19: "(1,3,4,5,6-penta-O-acetyl-2N-" should be --(1,3,4,5,6-penta-<u>O</u>-acetyl-2-N- --

Column 12, line 47: "lipds" should be --lipids--

UNITED STATES PATENT AND TRADEMARK OFFICE
CERTIFICATE OF CORRECTION

PATENT NO. : 4,851,511

DATED : July 25, 1989

INVENTOR(S) : Hakomori et al.

It is certified that error appears in the above-identified patent and that said Letters Patent is hereby corrected as shown below:

Column 12, line 63: "Clostridium" should be --<u>Clostridium</u>--

Column 12, lines 63-64: "Arthrobacter" should be --<u>Arthrobacter</u>--

Column 12, line 67: after "was" insert --directly--

Column 13, line 4: "glycolipds" should be --glycolipids--

Column 14, line 18: "Arthrobacter" should be --<u>Arthrobacter</u>--

Column 14, line 24: "Arthrobacter" should be --<u>Arthrobacter</u>--

Column 14, line 26: "Clostridium" should be --<u>Clostridium</u>--

Column 15, line 44: "HPTLC" should be --HPLC--

Column 15, line 62: "laconeotetraosylceramide" should be --lactoneotetraosylceramide--

Column 15, line 68: "acording" should be --according--

Column 16, line 9: "dissolved" should be --developed--

Column 16, lines 24-25: "disialosyllactotetraodylceramide" should be --disialosyllactotetraosylceramide--

Column 16, line 31: "fucosoyl" should be --fucosyl--

Column 16, line 53: after "radioimmunoassay" insert --with antibody dilution as well as antigen dilution. Solid-phase radioimmunoassay--

Column 16, line 58: "cholestrol" should be --cholesterol--

UNITED STATES PATENT AND TRADEMARK OFFICE
CERTIFICATE OF CORRECTION

PATENT NO. : 4,851,511
DATED : July 25, 1989
INVENTOR(S) : Hakomori et al.

It is certified that error appears in the above-identified patent and that said Letters Patent is hereby corrected as shown below:

Column 16, line 59: after "antibody" insert --was undiluted FH7 culture supernatant. I determining reactivies with antigen--
Column 17, line 10: "Disialostk LE$^a$" should be --disialosyl Le$^a$--
Column 17, line 11: "Soalidase" should be --Sialidase--
Column 17, line 19: "sialosy" should be --sialosyl--
Column 17, line 20: "antgen" should be --antigen--
Column 17, line 22: "Le$^a$" should be --anti-Le$^a$--
Column 17, line 34: "GlcNac" should be --GlcNAc--
Column 17, line 34: "GlcNacMe" should be --GlcNAcMe--
Column 18, line 57: after "showed" insert --less than 30%--
Column 19, line 2: "milignant" should be --malignant--
Column 19, line 13: "afterr" should be --after--
Column 19, line 32: "Processings" should be --Proceedings--
Column 19, line 39: "in vivo" should be --*in vivo*--
Column 19, line 57: "supresses" should be --suppresses--
Column 19, line 57: "in vivo" should be --*in vivo*--
Claim 2, line 4: "disialosy" should be --disialosyl--

UNITED STATES PATENT AND TRADEMARK OFFICE
CERTIFICATE OF CORRECTION

PATENT NO. : 4,851,511

DATED : July 25, 1989

INVENTOR(S) : Hakomori et al.

It is certified that error appears in the above-identified patent and that said Letters Patent is hereby corrected as shown below:

Claim 5, line 2: "specifivcally" should be --specifically--

Signed and Sealed this

Eighteenth Day of February, 1992

Attest:

HARRY F. MANBECK, JR.

*Attesting Officer*  *Commissioner of Patents and Trademarks*